US009211548B2

(12) United States Patent
Katsumoto (10) Patent No.: US 9,211,548 B2
(45) Date of Patent: Dec. 15, 2015

(54) APPARATUS FOR SAMPLE INTRODUCTION, CHIP FOR SAMPLE INTRODUCTION, AND METHOD FOR SAMPLE INTRODUCTION

(75) Inventor: Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 76 days.

(21) Appl. No.: 13/277,699

(22) Filed: Oct. 20, 2011

(65) Prior Publication Data

US 2012/0103814 A1 May 3, 2012

(30) Foreign Application Priority Data

Oct. 29, 2010 (JP) .................................. 2010-243270

(51) Int. Cl.
| | | |
|---|---|---|
| *G01N 27/447* | (2006.01) | |
| *G01N 27/26* | (2006.01) | |
| *B03C 5/00* | (2006.01) | |
| *B03C 5/02* | (2006.01) | |
| *G01N 15/10* | (2006.01) | |

(52) U.S. Cl.
CPC ................. *B03C 5/005* (2013.01); *B03C 5/026* (2013.01); *G01N 15/1031* (2013.01); *G01N 15/1056* (2013.01)

(58) Field of Classification Search
CPC .......... G01N 33/48721; G01N 33/487; G01N 33/4836; B03C 5/022
USPC ......... 204/406–409, 547, 643, 400, 450–453; 205/775, 792; 422/502; 435/288.5, 435/299.1
See application file for complete search history.

(56) References Cited

U.S. PATENT DOCUMENTS

| | | | | |
|---|---|---|---|---|
| 6,682,649 | B1 * | 1/2004 | Petersen et al. ............. | 205/777.5 |
| 7,250,775 | B1 * | 7/2007 | Collins et al. ................. | 324/692 |
| 2002/0063067 | A1 * | 5/2002 | Bech et al. .................... | 205/775 |
| 2007/0020146 | A1 * | 1/2007 | Young et al. ............... | 422/82.01 |
| 2007/0095669 | A1 * | 5/2007 | Lau et al. ....................... | 204/547 |
| 2007/0125941 | A1 * | 6/2007 | Lee et al. ...................... | 250/251 |

FOREIGN PATENT DOCUMENTS

JP     2010-181399        8/2010

OTHER PUBLICATIONS

Bacteria—Britannia Online Encyclopedia (http://www.britannica.com/EBchecked/topic/48203/bacteria), accessed Jan. 2, 2014.*
Garstecki et al. (Appl. Phys. Lett. 86:244108, 2005).*

* cited by examiner

*Primary Examiner* — Luan Van
*Assistant Examiner* — Steven Rosenwald
(74) *Attorney, Agent, or Firm* — K&L Gates LLP (57) ABSTRACT

The present disclosure provides an apparatus for sample introduction including a flow channel, a sample inlet, a metering unit, a separating unit, cell dischargers and, and a pressure controlling unit. The sample inlet is given a sample fluid such as blood. The sample inlet has a constricting hole that communicates with the flow channel for passage of a carrier fluid. The constricting hole has a diameter large enough for passage of a single cell contained in the sample fluid. The sample fluid is introduced into the flow channel through the constricting hole, and the cells in the sample fluid pass one by one through the constricting hole. The constricting hole does not exist inside the flow channel for passage of the carrier fluid, so that the diameter of the constricting hole does not affect the flow rate of the carrier fluid passing through the flow channel.

10 Claims, 6 Drawing Sheets

APPARATUS FOR SAMPLE INTRODUCTION, CHIP FOR SAMPLE INTRODUCTION, AND METHOD FOR SAMPLE INTRODUCTION

CROSS REFERENCES TO RELATED APPLICATIONS

The present application claims priority to Japanese Patent Application No. 2010-243270 filed on Oct. 29, 2010, the disclosure of which is incorporated herein by reference.

BACKGROUND

The present disclosure relates to a technology for apparatus, chip, and method for introduction of a cell-containing sample fluid taken from a patient into a flow channel through which a cell-carrying fluid flows.

Flow cytometry is one method of assay employed in the field of life science and medical research as well as in the field of medical treatment including clinical laboratory test. The analyte of flow cytometry is a fluid containing discrete cells. The sample fluid is caused to flow through a flow channel after dilution. The flow channel is equipped with a section for detecting signals from cells. Analysis of such signals permits identification of cell species contained in the sample fluid and counting of the number of cells.

Japanese Patent Laid-open No. 2010-181399 (Paragraphs [0041] to [0048], [0065] to [0071], and FIGS. 3 and 4) as shown below discloses an apparatus for dielectric cytometry that is designed to analyze cells based on the complex dielectric constant of cells. This apparatus includes a water flow unit, a measurement unit, a cell separation unit, and a control unit.

The water flow unit ejects the cell-containing fluid into the flow channel. The measurement unit acquires the complex dielectric constant of cells flowing through the flow channel and then calculates the dielectric parameter from the complex dielectric constant. The dielectric parameter identifies cell species contained in the fluid and counts the number of cells based on the fact that the dielectric parameter differs from one cell species to another. The cell separation unit separates the fluid flowing out of the measurement unit into two portions— one containing target cells and one to be discarded. The control unit establishes various set values for the water flow unit, measurement unit, and cell separation unit based on the information entered through the input interface.

The measurement unit includes the flow channel device having a flow channel for inflow, a flow channel for outflow, and a constricted part formed between the two flow channels. The two flow channels have their respective electrodes. After entry into the flow channel for inflow through the flow inlet, the cells pass one by one through the constricted part and then flow through the flow channel for outflow toward the flow outlet. The measurement unit measures current flowing across a pair of electrodes, calculates, based on the result of measurement, the complex dielectric constant for individual cells passing through the constricted part, and finally calculates the dielectric parameter from the resulting complex dielectric constant.

SUMMARY

The apparatus for dielectric cytometry disclosed in Japanese Patent Laid-open No. 2010-181399 (Paragraphs [0041] to [0048], [0065] to [0071], and FIGS. 3 and 4) is characterized in that the constricted part is formed inside the flow channel. The disadvantage of this structure is that the constricted part limits the flow rate of the cell-containing fluid, thereby causing cells to settle and stagnate in the flow channel.

It is desirable in an embodiment of the present disclosure to provide a technology for apparatus, chip, and method for introduction of a cell-containing sample fluid, the technology preventing cells from stagnating in the flow channel.

According to one embodiment of the present disclosure, the apparatus for sample introduction has a flow channel and a constricting hole.

The flow channel allows a carrier fluid to flow for cell transportation.

The constricting hole communicates with the flow channel, permits passage of a single cell, and allows the cell-containing sample fluid to flow into the flow channel.

The apparatus for sample introduction is provided in which the constricting hole does not exist inside the flow channel for passage of the carrier fluid. Thus the carrier fluid flows through the flow channel at any flow rate without being affected by the diameter of the constricting hole. This leads to a smooth flow that prevents cells from settling and stagnating in the flow channel.

The apparatus for sample introduction mentioned above may additionally have a pressure controlling unit.

This additional unit controls the pressure for passage of the carrier fluid, thereby controlling the flow rate of the carrier fluid passing through the flow channel and also controlling the flow rate of the sample fluid flowing into the flow channel through the constricting hole.

The apparatus for sample introduction is capable of controlling arbitrarily the flow rate of main stream (or the flow rate of the carrier fluid passing through the flow channel) and the flow rate of sample introduction (or the flow rate of the sample fluid entering the flow channel through the constricting hole).

The apparatus for sample introduction mentioned above may be additionally provided with a metering unit having a first pair of electrodes that generate an alternating current electric field at the position of the constricting hole.

The metering unit applies an alternating current voltage to the first pair of electrodes, thereby generating the alternating current electric field, so that the cells passing through the constricting hole are individually tested for complex dielectric constant.

The complex dielectric constant measured by the metering unit is used for detection of anomalous cells and separation of cells and other various objects. Being able to control the flow rate of the sample fluid entering the flow channel through the constricting hole, as mentioned above, the apparatus for sample introduction permits a single cell to pass through the constricting hole at a flow rate adequate for measurement of complex dielectric constant.

In the above-mentioned apparatus for sample introduction, the flow channel has branched flow channels formed at a position downstream of the constricting hole for separation of the cells.

In this case, the apparatus may be additionally provided with a separating unit having a second pair of electrodes.

The second pair of electrodes generate an electric field across the flow channel at the position downstream of the constricting hole and upstream of the branched flow channels.

The separating unit mentioned above applies a voltage to the second pair of electrodes, thereby generating an electric field, in response to the complex dielectric constant measured by the metering unit, so that the branched flow channels separate the cells.

The apparatus for sample introduction is designed such that the separating unit separates the cells, which have entered through the constricting hole, in response to the complex dielectric constant measured by the metering unit. Being able to control arbitrarily the flow rate of main stream and the flow rate of sample introduction, the apparatus for sample introduction prevents dispersion of cells at the position where the second pair of electrodes generate an electric field and also controls the separating speed as desired.

The above-mentioned apparatus for sample introduction may also be additionally provided with a stirring unit that stirs the sample fluid above the constricting hole before it flows into the flow channel through the constricting hole.

Owing to the stirring unit that stirs the cells in the sample fluid, the apparatus for sample introduction prevents the cells from settling in the sample fluid.

The stirring unit in the apparatus for sample introduction may be so designed as to generate an air stream to stir the sample fluid.

According to another embodiment of the present disclosure, the sample introduction chip has a substrate, a flow channel, and a constricting hole. The flow channel, which is formed on the substrate, permits passage of the carrier fluid for transportation of cells. The constricting hole, which is formed on the substrate, communicates with the flow channel, permits passage of a single cell, and permits the sample fluid containing the cell to enter the flow channel According to yet another embodiment of the present disclosure, the method for sample introduction permits the carrier fluid for transportation of cells to flow through the flow channel, and permits the sample fluid containing the cell to flow into the flow channel through the constricting hole that communicates with the flow channel and permits passage of a single cell.

As mentioned above, the present disclosure provides an apparatus for sample introduction that prevents cells from settling in the flow channel.

DETAILED DESCRIPTION

Embodiments of the present application will be described below in detail with reference to the drawings.

Given below is a description of the embodiments of the present disclosure.

<Overall Structure of the Apparatus for Dielectric Cytometry>

Figure 1:
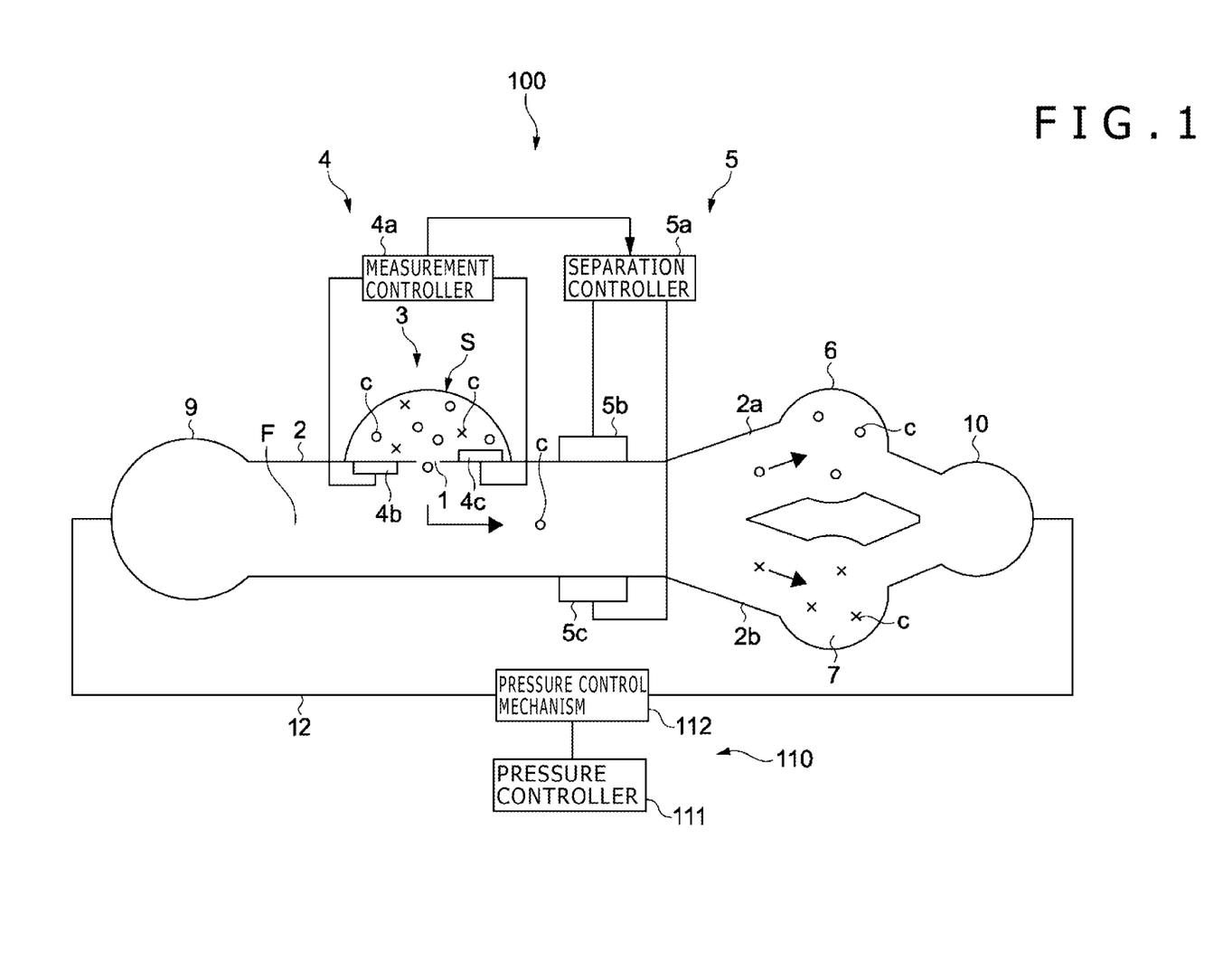
FIG. 1 is a schematic diagram illustrating the apparatus for dielectric cytometry (apparatus for sample introduction) according to one embodiment of the present disclosure.

FIG. 1 is a schematic diagram illustrating an apparatus for dielectric cytometry 100 (apparatus for sample introduction) according to one embodiment of the present disclosure.

As shown in FIG. 1, the apparatus for dielectric cytometry 100 includes a micro-flow channel 2 ("flow channel" for short hereinafter), a sample inlet 3, a metering unit 4, a separating unit 5, cell dischargers 6 and 7, and a pressure controlling unit 110.

The flow channel 2 permits the flow of the carrier fluid (F) that carries the cells (C). The carrier fluid (F) is typically a fluid that has the same characteristic properties as the medium (M) for the sample fluid (S) to be fed into the sample inlet 3. The flow channel 2 has a flow inlet 9 (into which the carrier fluid (F) flows), the branched flow channels 2a and 2b (through which the carrier fluid containing the cells (C) branches out), and a flow outlet 10 (from which the carrier fluid (F) flows out).

The carrier fluid (F) that flows into the flow inlet 9 is the one which is stored in a high-pressure fluid reservoir 113a of the pressure controlling unit 110. (See FIG. 2.) The carrier fluid (F) which flows out of the flow outlet 10 is stored in a low-pressure fluid reservoir 113b of the pressure controlling unit 110, which is placed downstream of the flow channel 2. (See FIG. 2.)

The sample inlet 3 is given the sample fluid (S) in the form of cell suspension, such as blood sampled from a patient, by dropping from a pipet 8. (See FIG. 4.) The sample inlet 3 has the constricting hole 1 communicating with the flow channel 2 through which the carrier fluid (F) flows. The constricting hole 1 has a diameter just large enough for passage of each of the cells (C) (such as red and white blood cells) contained in the sample fluid (S). The flow channel 2 is closed to the atmosphere at all parts except for the constricting hole 1.

Once put into the sample inlet 3, the sample fluid (S) enters the flow channel 2, through which the carrier fluid (F) flows, through the constricting hole 1. At this time, the cells (C) contained in the sample fluid (S) pass one by one through the constricting hole 1.

As shown in FIG. 1, the constricting hole 1 is placed outside the flow channel 2 through which the carrier fluid (F) flows, and hence its diameter has nothing to do with the flow rate of the carrier fluid (F) flowing through the flow channel 2. This structure, therefore, prevents the cells (C) from settling and stagnating in the flow channel 2.

The metering unit 4 has the first pair of electrodes 4b and 4c and a measurement controller 4a. The first pair of electrodes 4b and 4c are arranged at positions facing each other, with the restricting hole 1 held between them, in the sample inlet 3. The first pair of electrodes 4b and 4c are arranged such that one (4b) of them is inside the flow channel 2 and the other (4c) of them is outside the flow channel 2. The two electrodes 4b and 4c arranged in this manner generate a potential difference concentrating at the constricting hole 1.

FIG. 1 shows the constricting hole 1 and the first pair of electrodes 4b and 4c in different scales from actual sizes for clear presentation. In actual, the first pair of electrodes 4b and 4c are much smaller (in area) than the constricting hole 1. This applies also to FIG. 4 as explained later.

The measurement controller 4a applies an alternating current voltage to the first pair of electrodes 4b and 4c, thereby creating an alternating current electric field at the position of the constricting hole 1. During this process, the measurement controller 4a varies the frequency of the alternating current voltage over a range of 0.1 MHz to 50 MHz in which the individual cells (C) passing through the constricting hole 1 experience dielectric relaxation. More than three frequencies, typically 10 to 20 frequencies are selected.

The measurement controller 4a also measures current flowing across the first pair of electrodes 4b and 4c, thereby acquiring the complex resistance across the electrodes, so that the complex resistance gives the complex dielectric constant of the cells (C) at varied frequencies. The complex dielectric constant may be obtained in any manner. The thus measured complex dielectric constant will be used for separation of cells (C), detection of anomalous cells (C), presentation of dielectric spectra, and the like.

The separating unit 5 separates the cells (C) of several species, which have entered the flow channel 2 through the constricting hole 1, into two groups—one composed of desired cells (C), which is led to the cell discharger 6, and the other composed of undesired cells (C), which is led to the cell discharger 7. The separating unit 5 has the second pair of electrode 5b and 5c and the separation controller 5a. The second pair of electrodes 5b and 5c are arranged at the positions facing each other, with the flow channel 2 held between them. They are placed downstream of the constricting hole 1 and upstream of the branched flow channels 2a and 2b.

The separation controller 5a determines which cells (C) should be separated according to the complex dielectric constant measured by the metering unit 4. When the separation controller 5a determines that a specific cell (C) should be separated, it applies a voltage to the second pair of electrodes 5b and 5c, thereby generating an electric field in the flow channel 2, at the time when the specific cell (C) passes through the position where the second pair of electrodes 5b and 5c are arranged.

The cell (C) which has passed through the position where the second pair of electrodes 5b and 5c are arranged, with an electric field applied to the second pair of electrodes 5b and 5c, passes through the branched flow channel 2a and reaches the cell discharger 6. On the other hand, the cell (C) which has passed through the position where the second pair of electrodes 5b and 5c are arranged, with an electric field not applied to the second pair of electrodes 5b and 5c, passes through the branched flow channel 2b and reaches the cell discharger 7.

The pressure controlling unit 110 has a pressure control mechanism 112, which adjusts the pressure of the carrier fluid (F), and a pressure controller 111, which controls the pressure control mechanism 112. The pressure controlling unit 110 controls the pressure to flow the carrier fluid (F), thereby adjusting the flow rate of the carrier fluid (F) flowing through the flow channel 2 and the flow rate of the sample fluid (S) entering the flow channel 2 through the constricting hole 1.

<Pressure Controlling Unit and Micro-Flow Channel Chip>

Given below is a description of the pressure controlling unit 110 and the micro-flow channel chip 11 (or sample introduction chip) in the apparatus for dielectric cytometry 100.

Figure 2:
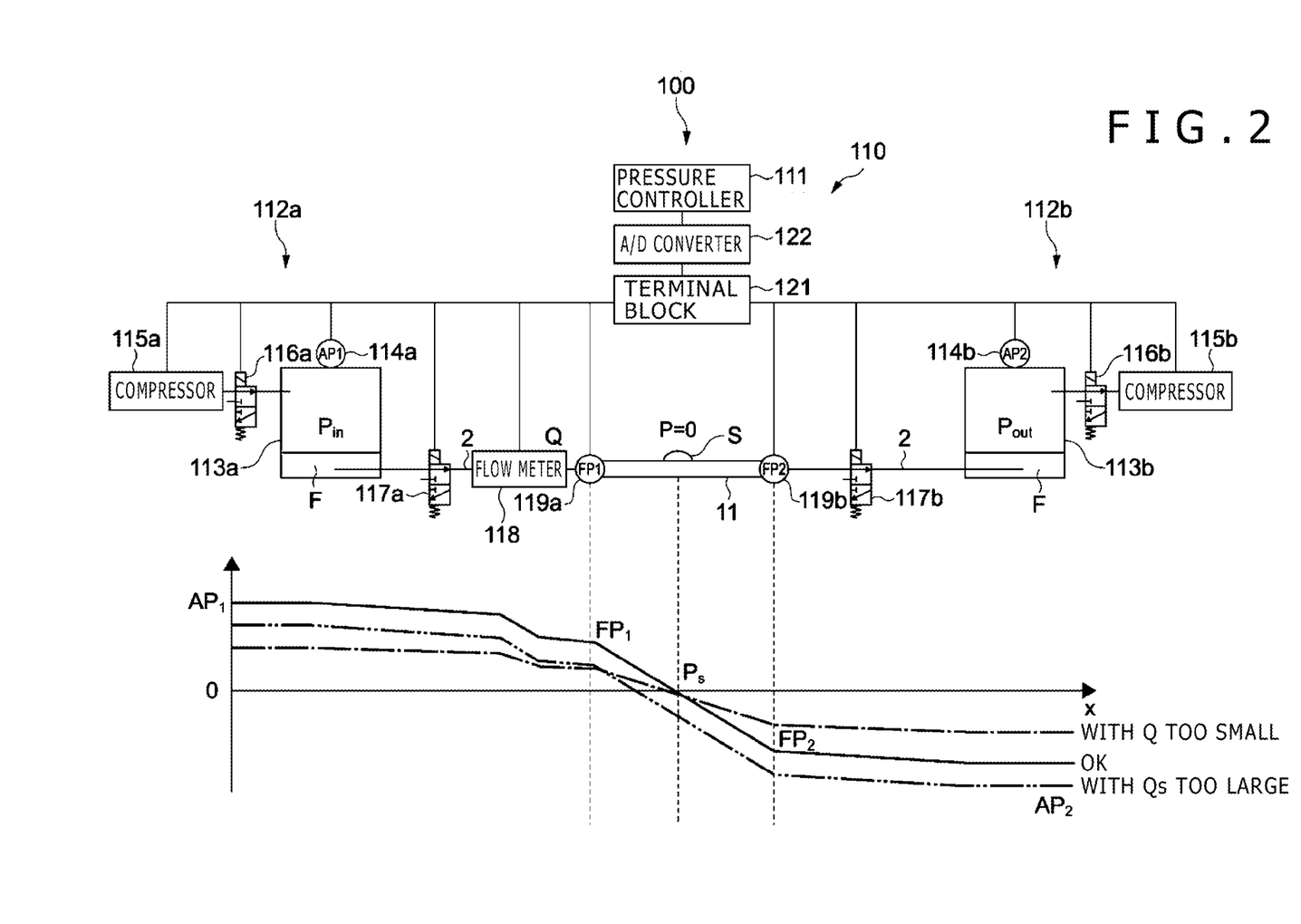
FIG. 2 is a diagram showing the pressure controller and a micro-flow channel chip (chip for sample introduction) in the apparatus for dielectric cytometry.
Figure 3:
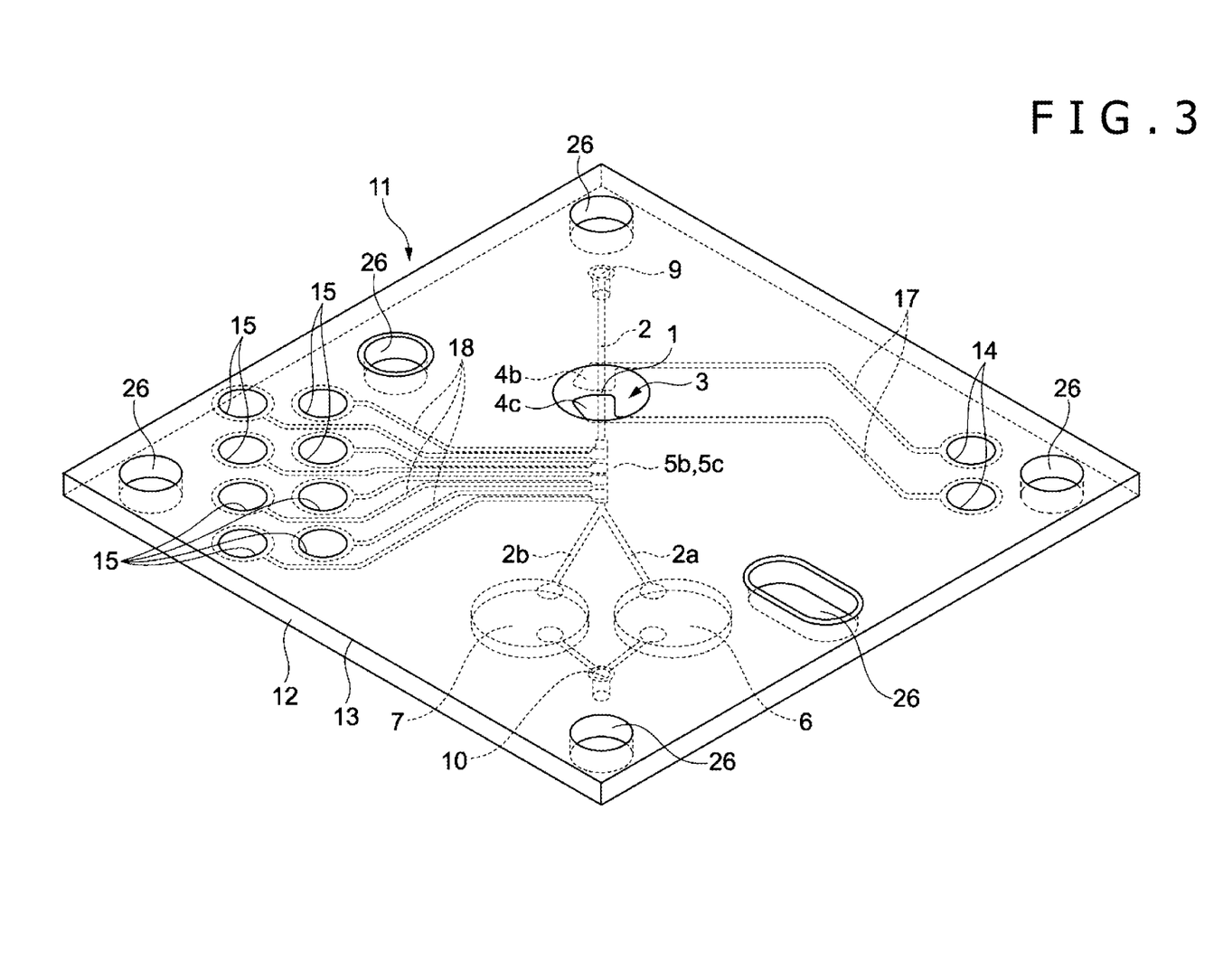
FIG. 3 is a perspective view showing the micro-flow channel chip.
Figure 4:
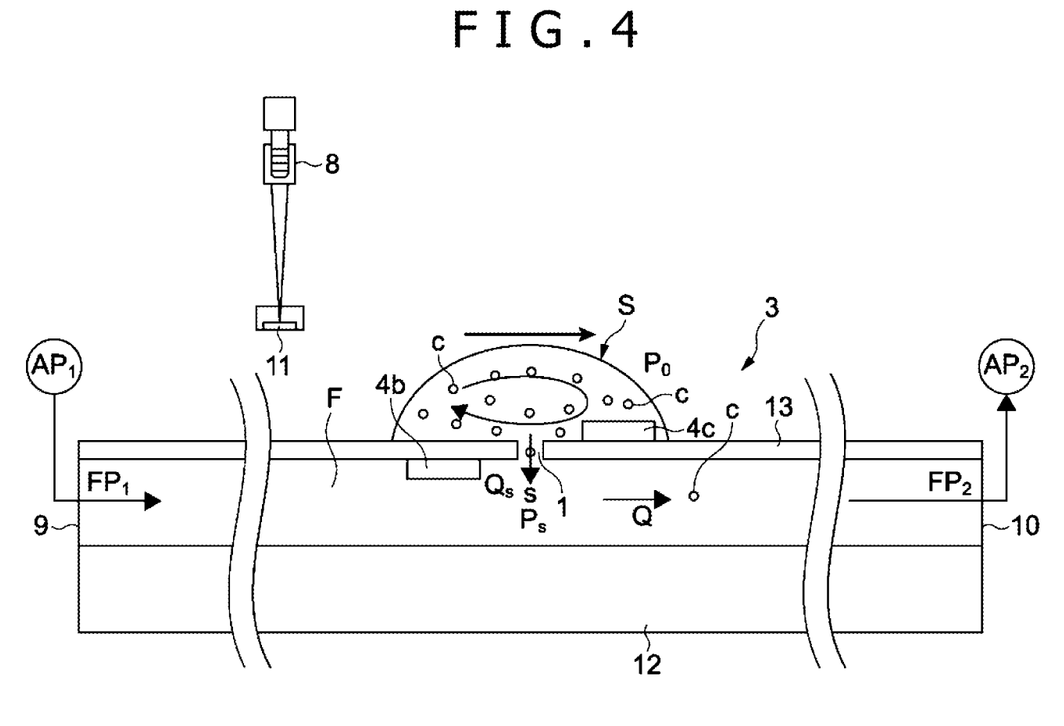
FIG. 4 is a sectional view showing the vicinity of the inlet of the micro-flow channel chip.

FIG. 2 is a diagram showing the pressure controlling unit 110 and the micro-flow channel chip 11 in the apparatus for dielectric cytometry 100. There are also shown in FIG. 2 gauge pressures at various parts in the apparatus for dielectric cytometry 100. FIG. 3 is a perspective view showing the micro-flow channel chip 11. FIG. 4 is a sectional view showing the vicinity of the sample inlet 3 of the micro-flow channel chip 11.

As shown in FIG. 2, the apparatus for dielectric cytometry 100 has the pressure controlling unit 110, which controls the pressure to flow the carrier fluid (F) through the flow channel 2, and the micro-flow channel chip 11 ("flow channel chip 11" for short hereinafter), which is detachable from the apparatus for dielectric cytometry 100.

The pressure controlling unit 110 has the first pressure control mechanism 112a, which controls the pressure of the carrier fluid (F) upstream of the flow channel 2, and the second pressure control mechanism 112b, which controls the pressure of the carrier fluid (F) downstream of the flow channel 2. The pressure controlling unit 110 also has the pressure controller 111 which controls the first pressure control mechanism 112a and the second pressure control mechanism 112b.

The first pressure control mechanism 112a includes the high-pressure fluid reservoir 113a, the first compressor 115a, and a first air valve 116a placed between them. Similarly, the second pressure control mechanism 112b includes the low-pressure fluid reservoir 113a, the second compressor 115b, and a second air valve 116b placed between them. In the system shown in FIG. 2, the first air valve 116a and the second air valve 116b are solenoid valves of 3-port 2-position type.

The high-pressure fluid reservoir 113a stores the carrier fluid (F) to be fed to the flow channel 2. The low-pressure fluid reservoir 113b stores the carrier fluid (F) discharged from the flow channel 2. The high-pressure fluid reservoir 113a and the low-pressure fluid reservoir 113b are respectively provided with atmospheric pressure sensors 114a and 114b, which detect the atmospheric pressure in the reservoir.

The high-pressure fluid reservoir 113a is provided with a first valve 117a at its downstream side. The low-pressure fluid reservoir 113b is provided with a second valve 117b at its upstream side. In the system shown in FIG. 2, the first and second air valves 117a and 117b are solenoid valves of 3-port 2-position type.

The first valve 117a is provided with a flow meter 118 at its downstream side. Also, the flow channel chip 11 is provided with pressure sensors 119a and 119b, which detect the pressure of the carrier fluid (F), at its inlet 9 and outlet 10, respectively.

The pressure controller 111 is electrically connected to the constituents of the pressure control mechanisms 112, the flow meter 118, and the pressure sensors 119a and 119b through a terminal block 121 and an A/D converter 122.

The pressure controller 111 controls the first compressor 115a and the first air valve 116a, thereby controlling the atmospheric pressure in the high-pressure fluid reservoir 113a. The pressure controller 111 also controls the second compressor 115b and the second air valve 116b, thereby controlling the atmospheric pressure in the low-pressure fluid reservoir 113b. This is the way of controlling the pressure of the carrier fluid (F) upstream and downstream of the flow channel 2.

In addition, the pressure controller 111 controls the first and second valves 117a and 117b, thereby controlling the carrier fluid (F) flowing out of the high-pressure fluid reservoir 113a and the carrier fluid (F) flowing into the low-pressure fluid reservoir 113b. The first and second valves 117a and 117b may be switched with each other according to need when the flow channel chip 11 is detached from the apparatus for dielectric cytometry 100.

The flow channel chip 11 is attached to and detached from the apparatus for dielectric cytometry 100 by means of a special jig (not shown) which serves as a casing for storage of the chip. In addition, the flow channel chip 11 may be replaced by another one when it is cleaned or when it needs to adapt itself to the varying size of cells (C) under examination.

As shown in FIGS. 3 and 4, the flow channel chip 11 includes a substrate 12 and a sheet-like member 13 formed thereon from a polymeric material. The substrate 12 has the flow inlet 9, the flow channel 2, the branched flow channels 2a and 2b, the cell dischargers 6 and 7, and the flow outlet 10, which are formed therein. The flow channel chip 11 also has grooves, etc. formed in the surface thereof, and it has its surface covered with the sheet-like member 13.

The sample inlet 3 is formed in the surface of the sheet-like member 13 at a lower level than other components so that the sample fluid (S), such as blood, placed in the sample inlet by the pipet 8 (shown in FIG. 4) will not flow out of it.

The sample inlet 3 has the constricting hole 1 at nearly the center thereof. The constricting hole 1 is a minute hole vertically penetrating through the sheet-like member 13.

The apparatus for dielectric cytometry 100 may be additionally provided with a stirrer (not shown) to stir the sample fluid (S) given to the sample inlet 3. The stirrer generates an air stream and blows it against the sample fluid (S) which is going to pass through the constricting hole 1. (See FIG. 4.) Thus, the cells (C) included in the sample fluid (S) is stirred by the air stream, so that the cells (C) is prevented from settling in the sample fluid (S).

The metering unit 4 has the first pair of electrodes 4b and 4c, which are arranged at positions facing each other, with the constricting hole 1 held between them, in the sample inlet 3. These two electrodes 4b and 4c are arranged on the back and front of the sheet-like member 13, respectively.

The first pair of electrodes 4b and 4c are electrically connected to the measurement controller 4a through wirings 17 and electrode pads 14. The first pair of electrodes 4b and 4c generate an alternating current electric field across the constricting hole 1 in response to signals from the measurement controller 4a.

The separating unit 5 has the second pair of electrodes 5b and 5c, which are arranged at the positions facing each other, with the flow channel 2 held between them in its widthwise direction, on the back of the sheet-like member 13. The second pair of electrodes 5b and 5c are electrically connected to the separation controller 5a through wirings 18 and electrode pads 15. The second pair of electrodes 5b and 5c generate an alternating current electric field across the flow channel 2 in response to signals from the separation controller 5a. The electric field induces a dielectric migration force in the cells (C) being transported through the flow channel 2 by the carrier fluid F, so that the desirable cells (C) flow toward the cell discharger 6.

The cell dischargers 6 and 7 are covered with the sheet-like member 13 in such a way that they permit the cells (C) to be taken out by the pipet 8 stuck through the sheet-like member 13.

The flow channel chip 11 has several holes 26 passing through it in its vertical direction. These holes 26 help the flow channel chip 11 to fit into its casing for storage.

(Regulation of the Flow Rate of Main Stream and the Flow Rate of Sample Introduction by Pressure Regulation of the Carrier Fluid (F))

The flow rate (Q) of main stream and the flow rate (Qs) of sample introduction are regulated by pressure regulation of the carrier fluid (F) as explained in the following. The flow rate (Q) of main stream is defined as the flow rate at which the carrier fluid (F) flows through the flow channel 2. The flow rate (Qs) of sample introduction is defined as the flow rate at which the sample fluid (S) flows into the flow channel 2 through the constricting hole 1. The following description refers to FIGS. 2 and 4.

It is assumed that the flow channel chip 11 is in such an initial state that the sample fluid (S) is not yet placed in the sample inlet 3 and the sample fluid (S) is not yet exist above (toward the atmosphere) the constricting hole 1. As the high-pressure fluid reservoir 113a and the low-pressure fluid reservoir 113b are pressurized to $AP_1$ and $AP_2$ ($AP_1 > AP_2$), respectively, the carrier fluid (F) begins to flow out of the high-pressure fluid reservoir 113a to flow through the flow channel 2 and enter the low-pressure fluid reservoir 113b. At this stage, the carrier fluid (F) flows at the flow rate (Q) of main stream.

It is assumed that $FP_1$ and $FP_2$ denote respectively the pressure at the flow inlet 9 and the flow outlet 10 of the flow channel chip 11. The pressures $FP_1$ and $FP_2$ determine the static pressure (Ps) at the position (s) just under the constricting hole 1. The static pressure (Ps) is induced by the pressure loss resulting from the line resistance that depends on the configuration of the flow channel 2 in the flow channel chip 11.

So long as the static pressure (Ps) is comparatively low and the sample fluid (S) does not exist above (toward the atmosphere) the constricting hole 1, the carrier fluid (F) does not flow out of the constricting hole 1 on account of its surface tension and air does not enter the flow channel 2.

Now, it is assumed that the sample inlet 3 is given the sample fluid (S), such as blood, which is a suspension of cells, in an amount of about 10 μL. In this state, the sample fluid (S) is in contact with the atmosphere and takes on a convex shape with a height of about 1 mm. Therefore, the sample fluid (S) above the constricting hole 1 is regarded as having the atmospheric pressure without static pressure. In addition, there exists no surface tension any longer at the constricting hole 1. Therefore, the sample fluid (S) enters the flow channel 2 owing to the pressure difference (0–Ps), where Ps denotes the static pressure at the position (s) just under the constricting hole 1. Thus, if the static pressure (Ps) is kept negative at the position (s) just under the constricting hole 1, the sample fluid (S) is drawn into the flow channel 2 of the flow channel chip 11.

Since the static pressure (Ps) is usually a function of line resistance, it may be expressed by the formula (1) below.

$$Ps = f(FP_1, FP_2) \tag{1}$$

Thus, the foregoing formula may be modified into the formula (2) below, in which Rs is a constant of proportionality, as long as the flow rate of sample introduction (Qs) has a sufficiently small Reynolds number.

$$Qs = Rs\, f(FP_1 - FP_2) \tag{2}$$

Incidentally, if the flow channel 2 in the flow channel chip 11 is formed such that the upstream side and the downstream side are hydrodynamically symmetric to each other with respect to the position (s) just under the constricting hole 1, the expression for the static pressure (Ps) at the position (s) is simplified to the formula (3) below.

$$Ps = (FP_1 + FP_2)/2 \tag{3}$$

In this case, the flow rate of sample introduction (Qs) may be expressed by the formula (4) below.

$$Qs = Rs(FP_1 + FP_2)/2 \tag{4}$$

The flow rate of main stream (Q) may also be expressed by the formula (5) below in terms of $FP_1$ and $FP_2$ by using the line resistance (R) of main stream.

$$Q = R(FP_1 - FP_2) \tag{5}$$

The foregoing suggests that arbitrary control is possible for the flow rate of main stream (Q) and the flow rate of sample introduction (Qs) by regulation of the pressure $AP_1$ in the high-pressure fluid reservoir 113a and the pressure $AP_2$ in the low-pressure fluid reservoir 113b for the adequate control of the pressures ($FP_1$ and $FP_2$) of the carrier fluid (F) at the upstream and downstream of the flow channel 2. It also suggests that the control of the $FP_1$ and $FP_2$ by the control of $AP_1$ and AP$_2$ permits the independent regulation of the flow rate of main stream (Q) and the flow rate of sample introduction (Qs).

For the purpose of experiment, there was prepared the flow channel chip 11 having the constricting hole 1 at the center of the flow channel 2. In the experiment, the flow rate of main stream (Q) and the flow rate of sample introduction (Qs) were measured, with the pressure AP$_1$ in the high-pressure fluid reservoir 113a controlled and the pressure AP$_2$ in the low-pressure fluid reservoir 113b controlled for regulation of the pressures FP$_1$ and FP$_2$ of the carrier fluid (F) at the flow inlet 9 and the flow outlet 10. Incidentally, the flow channel 2 of the flow channel chip 11 is 22 mm long, 200 μm wide, and 100 μm high. The carrier fluid (F) and the sample fluid (S) were substituted with pure water.

Figure 5:
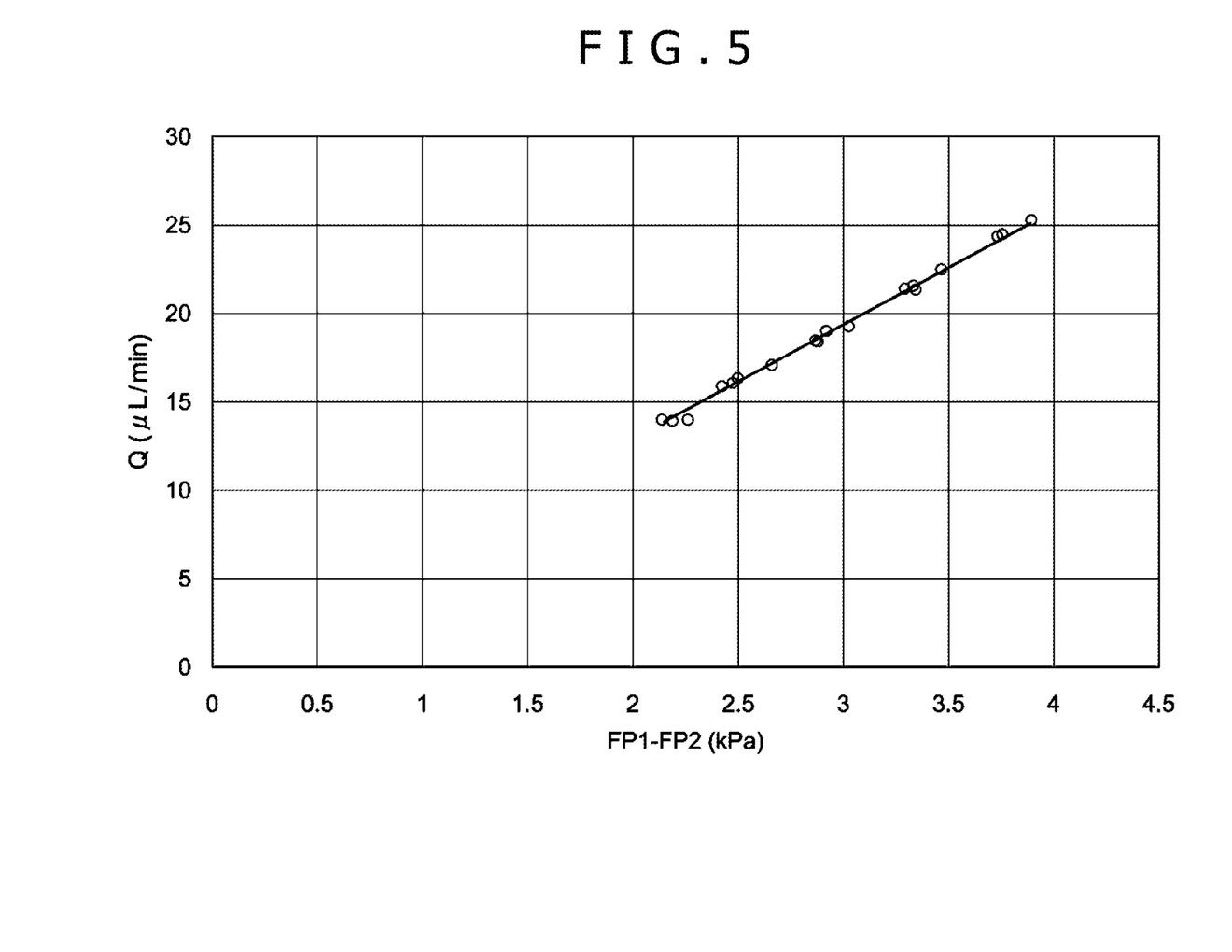
FIG. 5 is a graph illustrating the relationship between the flow rate of main stream and the difference between the pressures $FP_1$ and $FP_2$ of the carrier fluid at the inlet and outlet.
Figure 6:
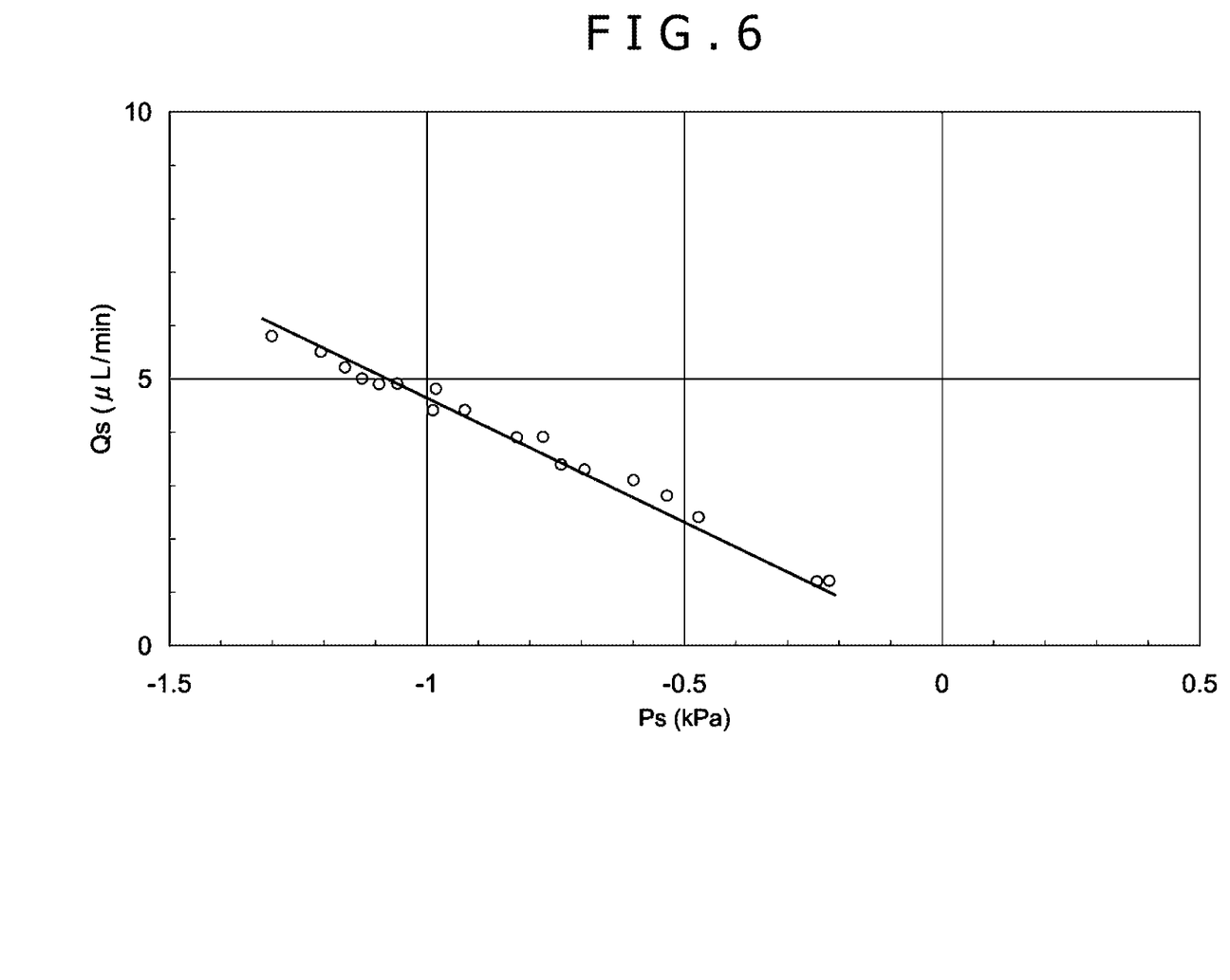
FIG. 6 is a graph illustrating the relationship between the static pressure and the flow rate of sample introduction, both measured at the position just under the constricting hole.

The experiment produced the results as shown in FIGS. 5 and 6. FIG. 5 is a graph showing the relationship between the difference in pressures (FP$_1$ and FP$_2$) and the flow rate of main stream (Q). FIG. 6 is a graph showing the relationship between the static pressure (Ps) at the position (s) just under the constricting hole 1 and the flow rate of sample introduction (Qs).

It is noted from FIG. 5 that there exists a linear relationship between the difference in pressures (FP$_1$ and FP$_2$) and the flow rate of main stream (Q). It is also noted from FIG. 6 that there exists a linear relationship between the static pressure (Ps) at the position (s) just under the constricting hole 1 and the flow rate of sample introduction (Qs). Incidentally, the foregoing experiment was able to independently regulate the flow rate of main stream (Q) and the flow rate of sample introduction (Qs) as the result of control over FP$_1$ and FP$_2$.

FIG. 2 shows the gauge pressure of the carrier fluid (F) in the flow channel 2. The solid line indicates that both the flow rate of main stream (Q) and the flow rate of sample introduction (Qs) are adequate because the difference between FP$_1$ and FP$_2$ is adequate and the magnitude of Ps is adequate. By contrast, the one-dot chain line indicates that the flow rate of main stream (Q) is too small because the difference between FP$_1$ and FP$_2$ is inadequate although the magnitude of Ps is adequate. Also, the two-dot chain line indicates that the flow rate of sample introduction (Qs) is too large because the magnitude of Ps is too large although the difference between FP$_1$ and FP$_2$ is adequate.

It is also noted from FIG. 2 that the flow rate of main stream (Q) and the flow rate of sample introduction (Qs) can be controlled independently and arbitrarily by controlling the pressures (FP$_1$ and FP$_2$) of the carrier fluid (F) at the upstream and downstream of the flow channel 2.

By the way, upon entrance into the flow channel 2 through the constricting hole 1, the cells (C) change their direction to the flow outlet 10. The cells (C) in the flow channel 2 become aligned within a certain range in the widthwise direction of the flow channel 2. And the degree of this alignment depends on the flow rate of main stream (Q) and the flow rate of sample introduction (Qs). How the cells (C) become aligned in the flow channel 2 in its widthwise direction was observed by means of the flow channel chip 11 which was used in the experiment to give the results shown in FIGS. 5 and 6. In this experiment, the cells (C) were substituted with polystyrene beads with a diameter of 10 μm. The experiment was run with the flow rate of main stream (Q) and the flow rate of sample introduction (Qs) controlled such that the polystyrene beads flowed through the flow channel 2 at a rate of 100 beads/sec in the separation unit 5. The alignment of the beads (in the widthwise direction) was observed at two positions 0 mm and 5 mm away from the constricting hole 1. It was found that the beads mostly existed at the center within a spread of ±10 μm in the widthwise direction.

<Effects and Functions>

The embodiment mentioned above is characterized in that the constricting hole 1 does not exist in the flow channel 2 for passage of the carrier fluid (F). Consequently, the constricting hole 1 has no effect, regardless of its diameter, on the flow rate of the carrier fluid (F) passing through the flow channel 2. The result is that the cells (C) smoothly pass through the flow channel 2 without settling and stagnation therein.

Now, it is assumed for comparison that a hypothetical apparatus with the constricted passage formed in the flow channel 2. This apparatus may be run on the principle of high-performance chromatography to prevent the cells (C) from settling in the flow channel 2. In this case, the cells (C) in the sample fluid (S) are transferred by the carrier fluid (F) in such a way that a dissimilar fluid (such as air) is held between the sample fluid (S) and the carrier fluid (F), with an interface (such as gas-liquid interface, when the dissimilar fluid is air) formed between them.

The interface formed between the sample fluid (S) and the dissimilar fluid and between the carrier fluid (F) and the dissimilar fluid leads to a complicated sequence of liquid transfer, which in turn necessitates the apparatus 100 for dielectric cytometry to have a complex structure. Moreover, in the case where air is used as the dissimilar fluid, there is the possibility of bubbles stagnating in the flow channel 2, and bubbles existing in the constricted passage prevent accurate measurement of complex dielectric constant for the cells (C).

This is not the case in this embodiment in which settling of the cells (C) in the flow channel 2 does not occur owing to the constricting hole 1 which communicates with the flow channel 2 for passage of the carrier fluid (F). Owing to its simple structure, the embodiment ensures a simple sequence of liquid transfer, which leads to cost reduction. In addition, the absence of bubbles in the constricting hole 1 permits accurate measurement of complex dielectric constant for the cells (C).

Being so designed as to control the pressures (FP$_1$ and FP$_2$) of the carrier fluid (F), this embodiment permits the flow rate of sample introduction (Qs) to be controlled at any value. The control in this manner permits the cells (C) to pass through the constricted hole 1 at individually controlled flow rates. This means that each of the cells (C) passes through the constricting hole 1 at a flow rate adequate for measurement of its complex dielectric constant at various frequencies.

Being so designed as to control the pressures (FP$_1$ and FP$_2$) of the carrier fluid (F), this embodiment permits the flow rate of main stream (Q) to be controlled at any value. The control in this manner permits the cells (C) entering the flow channel 2 to flow at any flow rate. The result is that the cells can be separated at any rate by the separating unit 5.

Being so designed as to control the pressures (FP$_1$ and FP$_2$) of the carrier fluid (F) and to control the flow rate of main stream (Q) and the flow rate of sample introduction (Qs), this embodiment prevents dispersion of the cells (C) entering the flow channel 2 through the constricting hole 1. Moreover, owing to its control over the flow rate of main stream (Q) and the flow rate of sample introduction (Qs), this embodiment permits the cells (C) to be separated at an adequate rate and to be aligned in an adequate manner.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An apparatus for sample introduction, comprising:
    a flow channel for passage of a carrier fluid to transport cells;
    a constricting hole that communicates with said flow channel, permits passage of a single cell, and allows a sample fluid containing said sample to flow into said flow channel; and
    a first pair of electrodes arranged at positions facing each other at a position of the constricting hole with the constricting hole between the first pair of electrodes,
    wherein a first one of the first pair of electrodes is located inside the flow channel and on only one side of the constricting hole, and a second one of the first pair of electrodes is located outside the flow channel and on only one side of the constricting hole that is an opposite side in plan view to the side on which the first one is formed, and
    further comprising a measurement controller that is configured to apply an alternating current to the first pair of electrodes while varying the frequency of said alternating current to enable dielectric relaxation of cells passing through the constricting hole.

2. The apparatus for sample introduction according to claim 1, further comprising
    a pressure controlling unit configured to control the pressure for passage of said carrier fluid, thereby regulating the flow rate of said carrier fluid passing through said flow channel, and regulating the flow rate of said sample fluid flowing into said flow channel through said constricting hole.

3. The apparatus for sample introduction according to claim 2, further comprising
    a metering unit configured to include the first pair of electrodes generating an alternating current electric field at the position of said constricting hole, the metering unit applying an alternating current voltage to said first pair of electrodes, thereby generating said alternating current electric field, for measurement of complex dielectric constant of individual cells passing through said constricting hole.

4. The apparatus for sample introduction according to claim 3, in which said flow channel has branched flow channels formed at the position downstream of said constricting hole for separation of said cells, the apparatus further comprising:
    a separating unit configured to include a second pair of electrodes generating an electric field across said flow channel at the position downstream of said constricting hole and upstream of said branched flow channels, the separating unit applying a voltage to said second pair of electrodes to thereby generate said electric field, in response to said complex dielectric constant measured by said metering unit, thereby separating said cells by use of said branched flow channels.

5. The apparatus for sample introduction according to claim 1, further comprising:
    a stirring unit configured to stir said sample fluid above said constricting hole before it flows into said flow channel through said constricting hole.

6. The apparatus for sample introduction according to claim 5, wherein said stirring unit generates an air stream to stir said sample fluid.

7. A sample introduction chip comprising:
    a substrate;
    a flow channel that is formed on said substrate and permits passage of a carrier fluid for transportation of cells;
    a constricting hole that is formed on said substrate, communicates with said flow channel, permits passage of a single cell, and permits a sample fluid containing said cell to flow into said flow channel; and
    a first pair of electrodes arranged at positions facing each other at a position of the constricting hole with the constricting hole between the first pair of electrodes,
    wherein a first one of the first pair of electrodes is located inside the flow channel and on only one side of the constricting hole, and a second one of the first pair of electrodes is located outside the flow channel and on only one side of the constricting hole that is an opposite side in plan view to the side on which the first one is formed, and
    further comprising a measurement controller that is configured to apply an alternating current to the first pair of electrodes while varying the frequency of said alternating current to enable dielectric relaxation of cells passing through the constricting hole.

8. The sample introduction chip according to claim 7, wherein the constricting hole is positioned between the first pair of electrodes such that a potential difference generated between the first pair of electrodes is concentrated at the constricting hole.

9. The apparatus for sample introduction according to claim 1, wherein the constricting hole is positioned between the first pair of electrodes such that a potential difference generated between the first pair of electrodes is concentrated at the constricting hole.

10. A method for sample introduction utilizing the apparatus of claim 1, comprising:
    permitting a carrier fluid that transports cells to flow through a flow channel; and
    permitting a sample fluid containing cells to flow into said flow channel through a constricting hole that communicates with said flow channel and permits passage of a single cell.

* * * * *